United States Patent [19]

Werner et al.

[11] Patent Number: 5,146,017

[45] Date of Patent: Sep. 8, 1992

[54] PROCESS FOR THE METATHESIS OF PARTLY FLUORINATED HYDROCARBONS

[75] Inventors: Konrad V. Werner, Garching; Karin Weiss, Bayreuth, both of Fed. Rep. of Germany

[73] Assignee: Hoechst Aktiengesellschaft, Frankfurt am Main, Fed. Rep. of Germany

[21] Appl. No.: 776,553

[22] Filed: Oct. 15, 1991

[30] Foreign Application Priority Data

Oct. 17, 1990 [DE] Fed. Rep. of Germany ....... 4032896

[51] Int. Cl.$^5$ ..................... C07C 17/24; C07C 17/28; C07C 21/18
[52] U.S. Cl. .................................... 570/143; 570/136; 570/153; 570/128
[58] Field of Search ................................ 570/153, 143

[56] References Cited

U.S. PATENT DOCUMENTS

4,269,780 5/1981 Banasiak ............................... 570/153

OTHER PUBLICATIONS

Feast, W. J. et al., Polymer 20:1182–1183 (1979).
Feast, W. J. et al., J. of Molecular Catalysis 8:277–296 (1980).
bin Alimuniar, A. et al., Polymer 27:1281–1288 (1986).
Blackmore, P. M. et al., Polymer 27:1296–1303 (1986).
Weiss, K. et al., J. or Organometallic Chem. 355:273–280 (1988).
Weiss, K. et al., Angew. Chem 101:75–77 (1989).
[Weiss, K. et al., Chem. Abstr. 110:134664t (1989)].

Primary Examiner—Joseph E. Evans

[57] ABSTRACT

A process is described for the reaction of at least one partly fluorinated alkene with catalysts containing tungsten complex compounds, at 10° to 200° C., if appropriate in the presence of at least one inert solvent. A mixture of a partly fluorinated alkene with another partly fluorinated alkene or with a non-fluorinated alkene can also be employed for the reaction. Longer-chain partly fluorinated compounds are thereby obtained which contain at least one internal C=C double bond. Ethylene or a short-chain alkene is furthermore produced and is separated off from the reaction mixture. The longer-chain partly fluorinated compounds are valuable intermediates and can be hydrogenated to give, for example, highly heat-resistant special lubricants.

12 Claims, No Drawings

PROCESS FOR THE METATHESIS OF PARTLY FLUORINATED HYDROCARBONS

DESCRIPTION

The invention relates to a process for the metathesis of partly fluorinated hyrocarbons which contain a double bond. It furthermore relates to alkenes which contain a central double bond and two terminal perfluoroalkyl groups.

The disproportionation of olefinic compounds, which can contain functional groups, under the action of heat and/or catalysts, which as a rule comprise transition metals, to form compounds which have a higher and lower molecular weight than the starting substance, called "metathese" since 1967, has been known for 25 years. Ring-opening polymerization of cycloolefins proceeds analogously to the metathesis of olefinic compounds.

The books "Olefin Metathesis and Ring-opening Polymerization of Cycloolefins" by V. Dragutan, A.T. Balaban and M. Dimonic, Editura Academici/Bucharest, 1981 and John Wiley & Sons/Chichester-New York, 1985 and "Olefin Metathesis" by K.J. Ivin, Academic Press/London-New York, 1983, contain detailed descriptions. Heterogeneous and homogeneous catalysts comprising compounds of transition metals, above all molybdenum, tungsten and rhenium, were used for the olefin metathesis. Simple binary and ternary catalyst systems containing metal compounds, such as oxides, sulfides and (halogen) salts, and also metal complex compounds, which comprise, for example, organic radicals and ligands, such as CO, or tertiary phosphines, are known. $Al_2O_3$ and $SiO_2$, for example, are used as supports for heterogeneous catalysts. Cl, Br and alkoxyalkyl, keto, amino, alkoxycarbonyl, carboxyl and cyano groups, for example, have been used as functional groups which the olefins carry. Co-metatheses of two different olefinic compounds or of an olefinic compound with a cycloolefinic compound are also known.

K. Weiss and M. Denzner, J. of Organometallic Chemistry, 355 (1988) pages 273 to 280 describe reaction products of tungsten (VI) carbyne complex compounds with surface chromium (II) compounds on silica gel as heterogeneous catalysts which are suitable for the metathesis of alkenes.

Reaction products of tungsten (VI) carbyne complex compounds with only silica gel are described as metathesis catalysts by K. Weiss and G. Lössel, Angew. Chemie, 101 (1989) pages 75 to 77 [C.A., Vol. 110 (1989), 134664t].

A number of publications by W.J. Feast and colleagues: Journ. of Molecular Catalysis, 8 (1980) pages 277 to 296; Polymer, 20 (1979) pages 1182 to 1183 and 27 (1986) pages 1281 to 1288 and pages 1296 to 1303 are concerned with ring-opening polymerization of hydrocarbon ring systems which are substituted by fluorine and/or trifluoromethyl groups away from the C=C double bond, homogeneous catalysts comprising tungsten being used, inter alia.

Nothing is known to data of the metathesis of open-chain, partly fluorinated alkenes.

The object of the invention is to provide a process which allows novel longer-chain compounds which comprise at least one —$CH_2$—CH=CH—$CH_2$— group and at least one fluorinated alkyl radical to be prepared from compounds which comprise a fluorinated alkyl radical and at least one —$CH_2$—CH=CH— group.

This object is achieved by a process for the reaction of optionally substituted hydrocarbons which contain at least one double bond using tungsten-containing catalysts, ethylene or an ethylene derivative being split off, to form longer-chain substituted hydrocarbons which contain at least one central double bond, at 10° to 200° C., if necessary in the presence of an inert solvent, under normal atmospheric pressure, reduced pressure or the autogenous pressure of the reaction mixture, which comprises using, for the reaction, at least one alkene of the formula

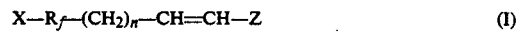

$$X—R_f—(CH_2)_n—CH=CH—Z \qquad (I)$$

or

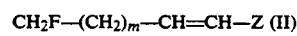

$$CH_2F—(CH_2)_m—CH=CH—Z \qquad (II)$$

in which $R_f$ is a straight-chain, branched or cyclic perfluoroalkylene radical having 1 to 18 carbon atoms, m and n are each an integer from 1 to 10, X is F, H, Cl, alkyl having 1 to 6 carbon atoms or aryl having 6 to 10 carbon atoms and Z is H, alkyl having 1 to 10 carbon atoms, arylalkyl having 7 to 11 carbon atoms, the radical —$(CH_2)_nR_fX$ or the radical —$(CH_2)_m$—$CH_2F$, in which, if only one compound is employed, this must have different substituents on the two sides of the —CH=CH— group.

Examples of compounds of the formula (I) which are suitable for carrying out the process according to the invention are:

$(CF_3)_2CF—(CH_2)_2—CH=CH_2$

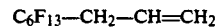

$C_6F_{13}—CH_2—CH=CH_2$

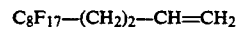

$C_8F_{17}—(CH_2)_2—CH=CH_2$

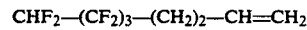

$CHF_2—(CF_2)_3—(CH_2)_2—CH=CH_2$

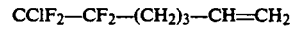

$CClF_2—CF_2—(CH_2)_3—CH=CH_2$

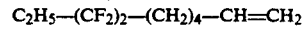

$C_2H_5—(CF_2)_2—(CH_2)_4—CH=CH_2$

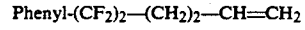

Phenyl-$(CF_2)_2$—$(CH_2)_2$—CH=$CH_2$

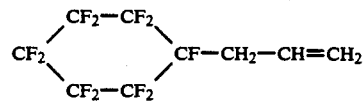

$C_4F_9$—$(CH_2)_2$—CH=CH—$(CH_2)_2C_4F_9$

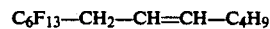

$C_6F_{13}$—$CH_2$—CH=CH—$C_4H_9$

$C_{12}F_{25}$—$(CH_2)_4$—CH=CH—$CH_2$—Phenyl

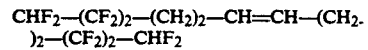

$CHF_2$—$(CF_2)_2$—$(CH_2)_2$—CH=CH—$(CH_2)_2$—$(CF_2)_2$—$CHF_2$

Examples of suitable compounds of the formula (II) are:

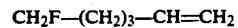

$CH_2F$—$(CH_2)_3$—CH=$CH_2$ $CH_2F-(CH_2)_6-CH=CH-C_2H_5$ $CH_2F-(CH_2)_8-CH=CH-CH_2-Phenyl$ $CH_2F-(CH_2)_2-CH=CH-(CH_2)_2-CH_2F$ One or more of the compounds of the formula(I) and (II) can be employed. If only a single compound is used, this must contain different substituents on the two sides of the —CH=CH— group. Compounds of the formula (I) in which $R_f$ is a perfluoroalkylene group having 2 to 10 carbon atoms, in particular having 3 to 8 carbon atoms, are preferably used. Those compounds of the formula (I) in which X is F are furthermore preferred. Compounds of the formula (I) in which n is an integer from 1 to 4, in particular 1 or 2, are furthermore preferred because of their good accessability and reactivity. The same applies to m in compounds of the formula (II). The substituent Z in the compound of the formula (I) or in the compound of the formula (II) is advantageously chosen so that the boiling point of its vinyl compound under normal atmospheric pressure is below the reaction temperature chosen and the substituent Z contains at least 2 carbon atoms less than the substituent $XR_f(CH_2)_n$13 in the compound of the formula (I) or $CH_2F(CH_2)_m$— in the compound of the formula (II). The substituent Z is preferably an alkyl radical having 3 or 4 carbon atoms, and in particular H, methyl or ethyl. Particularly good results are obtained if compounds of the formula (I) in which X is F and Z is H are employed.

In addition to one or more of the compounds of the formulae (I) and (II), compounds which do not contain fluorine, of the formula $$A-(CH_2)_t-CH=CH-E \quad (III)$$

in which
A is H, —CH$_2$Cl, aryl having 6 to 10 carbon atoms or —CH=CH$_2$,
t is an integer from 1 to 10 and
E is H, alkyl having 1 to 10 carbon atoms or arylalkyl having 7 to 11 carbon atoms,
in which the bonds at A and E can be closed to form a ring, can be employed.

Examples of compounds which are suitable for the process according to the invention are:

$CH_3-(CH_2)_7-CH=CH_2$ $CH_2Cl-CH_2-CH=CH_2$

Phenyl—$CH_2-CH=CH_2$ $CH_2=CH-(CH_2)_2-CH=CH_2$ $CH_2Cl-CH_2-CH=CH-CH_2-CH_2Cl$ Phenyl-$CH_2-CH=CH-CH_2$—Phenyl $CH_3-(CH_2)_4-CH=CH-CH_3$ $CH_3-(CH_2)_7-CH=CH-(CH_2)_7-CH_3$

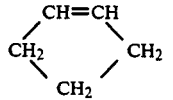 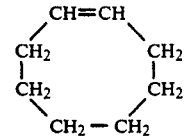

Compounds in which the substituent E is chosen so that the boiling point of its vinyl compound under atmospheric pressure is below the reaction temperature chosen and the substituent E contains at least 2 carbon atoms less than the substituent A—(CH$_2$)$_t$— are preferably used. The substituent E is preferably an alkyl radical having 3 or 4 carbon atoms, and in particular H, methyl or ethyl. If A is CH$_2$=CH—, oligomeric products of greater chain length which are formed by reacting 2 or more mol of the compound of the formula (III) with 1 or 2 mol of the compound of the formula (I) can be obtained. Compounds of the formula (III) in which A is CH$_2$=CH— and E is H are advantageously employed for such reactions.

In the reaction according to the invention, ethylene is split off if all the compounds of the formulae (I), (II) and (III) employed contain a —CH=CH$_2$ group, and ethylene can be split off if at least one of the compounds of the formulae (I), (II) or (III) employed contains a —CH=CH$_2$ group. If this is not the case, alkenes which are substituted by an organic radical on the two sides of the —CH=CH— group are split off. In the case of mixtures of starting substances which contain both the —CH=CH$_2$ group and the —CH=CH— group substituted on both sides, alkenes —CH=CH$_2$ substituted on one side can also be split off.

The reaction according to the invention takes place in the presence of catalysts comprising tungsten. Catalysts which are particularly suitable in this context are, for example, complex compounds of the formula $$\begin{array}{c} L_s^1 \\ | \\ R_3-W\equiv C-R^4 \\ | \\ L_s^2 \end{array} \quad (IV)$$

in which
R$_3$ is Cl, —CH$_2$—C(CH$_3$)$_3$, —O—C(CH$_3$)$_3$, —S—C(CH$_3$)$_3$ or —NG$_2$, in which G is an alkyl group having 1 to 4 carbon atoms or the benzyl radical,
R$^4$ is a straight-chain, branched or cyclic alkyl group having 1 to 6 carbon atoms, a trialkylsilyl group, the alkyl radicals of which each comprise 1 to 3 carbon atoms, or a benzyl, phenyl, tolyl or naphthyl group,
L$^1$ is a trialkylphosphine, trialkylphosphine oxide or ethylene glycol dialkyl ether, the alkyl groups of which contain 1 to 4 carbon atoms,
L$^2$ is a trialkylphosphine, trialkylphosphine oxide, trialkylphosphonium chloride or tetraalkylammonium chloride, the alkyl groups of which contain 1 to 4 carbon atoms, with the proviso that R is Cl if L$^2$ is a trialkylphosphonium or tetraalkylammonium chloride, and
is zero or 1.
Examples of such tungsten-containing catalysts are:

$(CH_3OCH_2CH_2OCH_3)Cl_3W\equiv C-C(CH_3)_3$

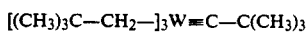

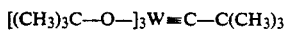

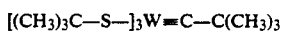

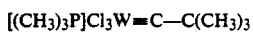

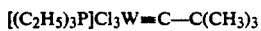

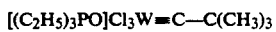

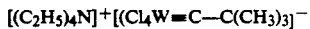

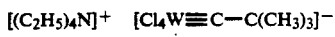

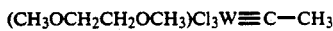

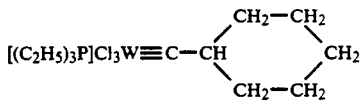

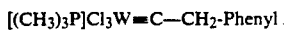

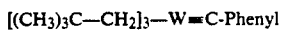

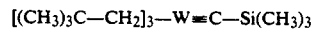

The preparation of such tungsten complex compounds is described by R.R. Schrock, D.N. Clark, I. Sancho, I.H. Wengrovius, S.M. Rocklage and S.F. Pedersen in "Organometallics", 1 (1982), pages 1,645 to 1650.

The tungsten complex compounds mentioned can be added as such to the liquid compounds of the formulae (I) and/or (II) and also to liquid mixtures thereof with one or more compounds(s) of the formula (III). However, solvents are preferably added. Solvents which are suitable here are liquid, saturated hydrocarbons, such as hexane, heptane, octane, isomer mixtures thereof and chlorine or fluorine substitution products thereof, such as propyl chloride, butyl chloride cyclohexyl chloride, methylene chloride, dichloroethane, dichloropropane, chloroform, trichloroethane, carbon tetrachloride, trichlorofluoromethane and trichlorotrifluoroethane.

In addition to the tungsten compounds, metal-alkyls, such as $Sn(CH_3)_4$, alkyl metal halides, such as $(C_2H_5)_2AlCl$, metal halides, such as $SNCl_4$ and $TiCl_4$, and aliphatic alcohols or phenols can additionally be employed as cocatalysts.

Catalysts which are built up from a solid support which essentially consists of silicon dioxide, aluminum oxide or mixtures of these two oxides and onto which a tungsten complex compound which contains a bond between tungsten and a carbon atom is bonded via oxygen atoms of the oxides mentioned or via chromium, which is bonded to these oxygen atoms, are furthermore particularly suitable catalysts.

It is assumed that the following structures are formed here:

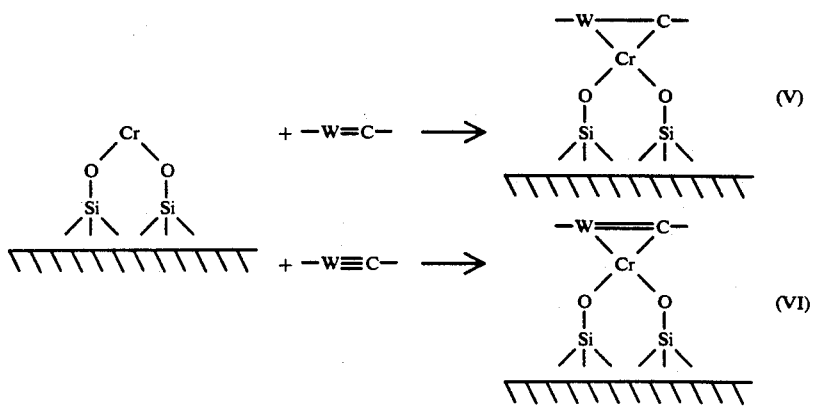

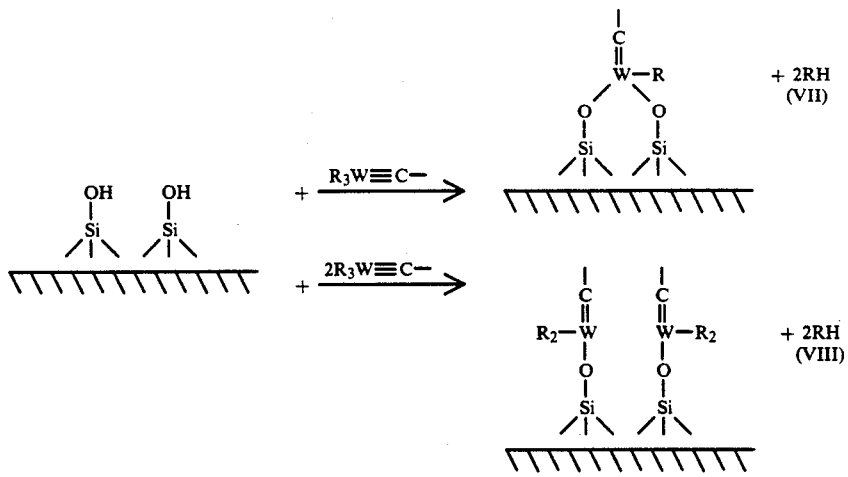

Particularly suitable tungsten compounds of the type R₃W≡C— are the compounds of the formula (IV) which are described above in more detail and which have a better storage stability and often also become even more active by bonding to the solid support. Such catalysts are described by K. Weiss and G. Lössel in "Angewandte Chemie", 101 (1989), pages 75 to 77.

Suitable tungsten compounds of the type —W≡C— are, for example, compounds of the following formula:

$$(CO)_yQW\equiv C-R^5 \quad (IX)$$

in which
Q is Cl, Br or I and
y is 4 or
Q is cyclopentadienyl, phenyl or naphthyl and
y is 2, and
R⁵ is a straight-chain, branched or cyclic alkyl group having 1 to 6 carbon atoms, phenyl, naphthyl or —NT₂, in which T if an alkyl group having 1 to 4 carbon atoms.
Examples of suitable compounds are:

(CO)₄ClW≡C-Phenyl (CO)₄BrW≡C-Phenyl (CO)₂Cyclopentadienyl-W≡C-Phenyl (CO)₂-Phenyl-W≡C—C(CH₃)

(CO)₄ClW≡C—C₂H₅

(CO)₂-Cyclopentadienyl-W≡C—N(CH₃)₂ the addition products of which on the solid supports given above in more detail, see formula (VI), are described by K. Weiss and M. Denzner in "Journal of Organometallic Chemistry", 355 (1988), pages 273 to 280.

Tungsten compounds of the type —W≡C— which are furthermore suitable are, for example, compounds of the following formula $$(CO)_5W=CR^1R^2 \quad (X)$$

in which
R¹ is alkyl having 1 to 10 carbon atoms, benzyl, phenyl or naphthyl, in which the aromatic ring of these radicals in turn can be substituted by 1 to 3 alkyl groups, which in turn together contain 1 to 12 carbon atoms, and
R² is alkyl having 1 to 10 carbon atoms, alkoxy having 1 to 6 carbon atoms or benzyl, phenyl, naphthyl, phenoxy or naphthoxy, in which the aromatic ring of these radicals in turn can be substituted by 1 to 3 alkyl groups, which in turn together contain 1 to 12 carbon atoms.

In the reaction of the compounds of the formula (X) with the chromium (II)-containing solid support, which essentially consists of silicon dioxide, aluminum oxide or mixtures of these two oxides, CO is split off, so that compounds of the formula

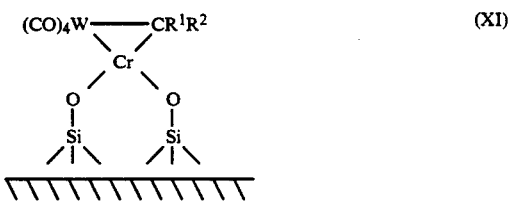

are formed. The preparation of such solid catalysts is described by K. Weiss, W. Guthmann and S. Maisuls in "Angewandte Chemie", 100 (1988), pages 268 to 270.

In the above comments, the term "silicon dioxide, aluminum oxide or mixtures of these two oxides" includes not only physical mixtures but also chemically bonded mixed oxides or alumosilicates.

The catalysts which are built up from solid supports and are described in the above paragraphs can be used as such and also as a suspension of small particles in solvents, for example the hydrocarbons described above, which can be chlorinated or fluorinated. If the compound(s) of the formula (I) or (II), if appropriate together with a compound of the formula (III), is present in the gas phase at the reaction temperature chosen, the catalysts built up from solid supports can be used in finely divided, fluidized form or as a fixed bed.

In general, 0.01 to 2 mol, preferably 0.1 to 1 mol, of tungsten compound per 100 mol of one or more compounds of the formulae (I), (II) and (III) are employed in the catalyst, but the amount of tungsten compound can also be more than 2 mol per 100 mol of compounds of the formulae (I), (II) and (III), especially if catalysts which are built up from solid supports are used.

The mixing ratio of the compounds of the formulae (I) or (II) with one another or with one or more of the compounds of the formula (III) can vary within wide limits. In general, 0.5 to 3 mol, preferably 1 to 2 mol, of the compound of the formula (III) is used per mol of the compound of the formula (I) or of the formula (II).

The reaction according to the invention is carried out at 10° to 200° C., below 10° C. the reaction in general proceeds too slowly and above 200° C. too many undesirable byproducts are formed. The choice of an optimum temperature depends on the heat stability of the starting substances and catalysts employed and of the end products to be achieved. Temperatures of 30° to 150° C. and in particular 50° to 120° C. are advantageously used.

The reaction is in general carried out under normal atmospheric pressure or the autogenous pressure of the reaction mixture. If the enthylene derivative split off in the reaction according to the invention has a relatively low volatility, it is advisable to use a reduced pressure and if appropriate higher-boiling solvents. The removal of the ethylene derivative split off can be accelerated by passing an inert gas, for example nitrogen or argon, through or over the reaction mixture. The ethylene or ethylene derivative driven off in gaseous form can either be disposed of, for example by combustion, or recovered by adsorption onto a suitable medium or by condensation.

Reaction mixtures which comprise exclusively compounds of low volatility can be separated by chromatography, if appropriate after dilution with a suitable solvent.

The higher molecular weight reaction product which remains after removal of the reaction products of lower molecular weight is separated and purified from any solvent present by fractional distillation, if appropriate under reduced pressure. In gas phase processes, the higher molecular weight reaction product is advantageously obtained by fractional condensation, and the same applies to unreacted starting substances, which can be recycled to the process.

The time for the reaction according to the invention can vary within wide limits. It depends on the starting substances, the catalyst and the reaction temperature. In general, the reaction has ended when no further ethylene or low molecular weight ethylene derivative can be separated off. Reaction times of 2 to 40 hours are usually sufficient for a discontinuous procedure.

During the reaction according to the invention, the reaction mixture is advantageously constantly mixed thoroughly, especially if a finely divided solid catalyst is employed. This mixing can be effected, for example, by stirring, shaking, pumping in circulation, boiling, evolution of gas from the reaction mixture or passing an inert gas through the reaction mixture.

The invention also relates to novel compounds of the formula

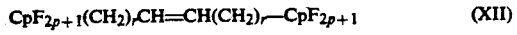

$$C_pF_{2p+1}(CH_2)_rCH=CH(CH_2)_r-C_pF_{2p+1} \quad (XII)$$

in which
p is a number from 2 to 10, preferably 3 to 8, and
r is a number from 1 to 4, preferably 1 to 2.

These compounds are prepared, for example, by the novel process described above, wherein a compound of the formula

$$XR_f-(CH_2)_n-CH=CH-Z \quad (I)$$

in which
X is F,
Z is H,
$R_f$ is a straight-chain or branched perfluoroalkylene radical having 2 to 10 carbon atoms and
n is an integer from 1 to 4,
is advantageously exclusively employed.

The longer-chain compounds which are obtainable by the novel process and contain at least one fluorinated alkyl radical and at least one —CH$_2$—CH=CH—CH$_2$— group are, because of their reactive double bond, particularly accessible to various other reactions which lead to useful substances. If, for example, the double bond is hydrogenated, products which can be used as heat-resistant lubricants are formed; they are also suitable as lubricating waxes for sports purposes )skis, sleds) where, in contrast to completely fluorinated hydrocarbons, they also have a certain miscibility with nonfluorinated paraffins. Compounds with shorter fluorinated alkyl radicals are soluble in mineral oils and can be used as corresponding additives. The double bond can be converted into an epoxide compound, for example with organic peracids, such as metachloroperoxybenzoic acid, which is in turn accessible to further reactions. It can thus be converted into the diol, the OH groups of which are suitable for the formation of simple esters or polyesters. The reaction according to the invention of partly fluorinated alkenes with dienes, such as 1,6-hexadiene, leads to oligomeric or polymeric compounds which contain several double bonds and have elastomeric character. These elastomers are crosslinkable, heat-stable plastics being formed.

The reaction according to the invention enables the formation of longer-chain compounds having partly fluorinated radicals, which would otherwise be accessible only via more cumbersome procedures, which often require several reaction steps.

The following examples are intended to illustrate the invention.

EXAMPLE 1

2 ccm (12 mmol) of 4-(perfluoroisopropyl) -1-butene and 200 mg of a solid finely divided catalyst which has been obtained by reaction of a solid silicon dioxide-chromium-(II) catalyst with the compound (CO)$_4$Cl-W≡C-phenyl, as described in "Journal of Organometallic Chemistry", 355 (1988), page 279, are introduced into a glass flask of 10 ccm capacity under dry nitrogen. The catalyst contains 0.022 mmol of tungsten compound. 0.18 mol of tungsten compound per 100 mol of 4-(perfluoroisopropyl)-1-butene are employed. The mixture is shaken at 76° C. for 7 hours, subsequently cooled and mixed with 10 ccm of pentane, and the solid catalyst is decanted off. The catalyst is shaken with a further 5 ccm of pentane and the liquid is decanted again, combined with the main amount and filtered over a layer of finely divided aluminum oxide 1 cm high. The solvent and unreacted 4-(perfluoroisopropyl)-1-butene are distilled off from the filtrate under 12 mbar (1.2 kPa) and 2020 C. The residue is distilled under normal atmospheric pressure, and the main portion passes over at 153° C. and has a density of 1.56 g/cm$^3$. The following signals are obtained by $^{13}$C and $^{19}$F nuclear magnetic resonance spectroscopy (NMR) in CDCl$_3$, based on tetramethylsilane and perfluoroacetic acid:

$^{13}$C-NMR (ppm): 121.4 CF$_3$; 91.3 CF; 28.9 CH$_2$; 24.6 and 19.5 CH$_2$—(C=); 129.5 and 128.8 —HC=CH— (cis, trans)

$^{19}$F-NMR (ppm): −1.84; −1.12 and −1.18 CF$_3$.

As analysis confirms, the main portion consists of 1,6-bis-(perfluoroisopropyl)-3-hexene

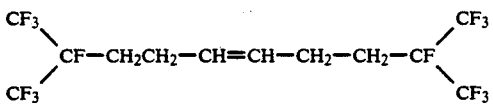

1.9 g =4.5 mmol =75% of the theoretical value are obtained. (The yield is lower than that determined by gas chromatography. A loss of substance by absorption has probably occurred due to filtration over Al$_2$O$_3$.)

EXAMPLE 2

250 g (0.028 mmol, based on the tungsten compound) of the solid catalyst described in Example 1 are suspended in 10 ccm of hexane at room temperature in a glass flask of 20 ccm capacity under dry nitrogen, the suspension is heated to 69° C., 1.3 ccm (5.54 mmol) of the compound C$_6$F$_{13}$CH—CH=CH$_2$ are added and the mixture is shaken at 69° C. for 7 hours. 0.5 mol of tungsten compound is employed per 100 mol of C$_6$F$_{13}$CH—CH=CH$_2$. The decrease in the starting substance and the increase in the reaction product are monitored by gas chromatography during the reaction. The reaction product is characterized as C$_6$F$_{13}$CH$_2$CH=CHCH$_2$ C$_6$F$_{13}$ by analysis by gas chromatography with direct subsequent analysis by mass spectroscopy (GC/MS analysis). The total conversion of the starting substance after 7 hours is 93.5% (based on 100% possible conversion). 71.4 mol of the starting alkene are reacted per hour and per mol of tungsten compound.

EXAMPLE 3

The procedure is analogous to Example 2, but 220 mg (0.025 mmol, based on the tungsten compound) of the solid catalyst described in Example 1 are employed without a solvent, 5.8 ml (24.4 mmol) of C$_6$F$_{13}$CH$_2$CH=CH are added and the mixture is shaken at 122° C. for 7 hours. 0.1 mol of tungsten compound is employed per 100 mol of C$_6$F$_{13}$CH—CH=CH$_2$. The reaction product is characterized as C$_6$F$_{13}$CH$_2$CH=CHCH$_2$ C$_6$F$_{13}$. The total conversion of the starting substance is 16.9% after 7 hours (based on 100% conversion). 160.0 mol of the starting alkene are reacted per hour and per mol of tungsten compound.

EXAMPLE 4

The procedure is analogous to Example 2. 230 mg (0.026 mmol, based on the tungsten compound) of the solid catalyst described in Example 1 are suspended in 10 ccm of hexane at room temperature, the suspension is heated to 69° C., 1.3 ccm (5.1 mmol) of the compound C$_6$F$_{13}$CH$_2$CH$_2$CH=CH$_2$ are added and the mixture is shaken at 69° C. for 7 hours. 0.5 mol of tungsten compound is employed per 100 mol of C$_6$F$_{13}$CH$_2$CH$_2$CH=CH$_2$. The reaction product is characterized as C$_6$F$_{13}$CH$_2$CH$_2$CH=CHCH$_2$ CH$_2$C$_6$F$_{13}$ by GC/MS analysis. The total conversion of the starting substance is 43.7% after 7 hours (based on 100% conversion). 37.6% mol of the starting alkene are reacted per hour and per mol of tungsten compound.

EXAMPLE 5

The procedure is analogous to Example 2. 45 mg (0.1 mmol) of the compound (CH$_3$OCH$_2$CH$_2$OCH$_3$)Cl$_3$W≡C—C(CH$_3$)$_3$, prepared as described in "Organometallics", Volume 1, No. 12 (1982), page 1,649, right-hand column, are dissolved in 10 ccm of 1,2-dichloroethane at room temperature, 11.2 g (50 mmol) of (CF$_3$)$_2$CF—CH$_2$CH$_2$CH=CH$_2$ are added and the mixture is shaken at 76° C. for 24 hours. 0.2 mol of tungsten compound is employed per 100 mol of (CF$_3$)$_2$CFCH$_2$CH$_2$CH=CH$_2$. The reaction product is characterized as (CF$_3$)$_2$CFCH$_2$CH$_2$CH=CHCH$_2$CH$_2$CF(CF$_3$)$_2$ by GC/MS analysis. The total conversion of the starting substance is 63.4% after 24 hours (based on 100% possible conversion). 44 mol of the starting alkene are reacted per hour and per mol of tungsten compound.

EXAMPLE 6

The procedure is analogous to Example 2. 150 mg (0.029 mmol, based on the tungsten compound) of a solid, finely divided catalyst obtained by reaction of a solid silicon dioxide catalyst with the compound [(CH$_3$)$_3$C—CH$_2$—]$_3$W≡C—C(CH$_3$)$_3$, as described in "Angewandte Chemie", 101 (1989), page 76, are suspended in 10 ml of heptane at room temperature, the suspension is heated to 69° C., 1 ccm (5.78 mmol) of the compound (CF$_3$)$_2$CFCH$_2$CH$_2$CH=CH$_2$ is added and the mixture is shaken at 69° C. for 7 hours. 0.5 mol of tungsten compound is employed per 100 mol of (CF$_3$)$_2$CF—CH$_2$CH$_2$CH=CH$_2$. The reaction product is characterized as (CF$_3$)$_2$CFCH$_2$CH$_2$CH=CHCH$_2$CF(CF$_3$)$_2$ by GC/MS analysis. The total conversion of the starting product is 88.1% (based on 100% possible conversion). 260.8 mol of the starting alkene are reacted per hour and per mol of tungsten compound.

EXAMPLE 7

The procedure is as described in Example 6, with the difference that no heptane is used and instead of 1 ccm, 5.1 ccm (28.9 mmol) of the compound (CF$_3$)$_2$CFCH$_2$CH$_2$CH=CH$_2$ are employed, in which the solid catalyst is suspended. The reaction is carried out at 76° C. for 7 hours. 0.1 mol of the tungsten compound is employed per 100 mol of the compound (CF$_3$)$_2$CFCH$_2$CH$_2$CH=CH$_2$. The reaction product is the same as in Example 6; the total conversion of the starting substance after 7 hours is 94.4% (based on 100% conversion). 1,240 mol of the starting alkene are reacted per hour and per mol of tungsten compound.

EXAMPLE 8

The procedure is analogous to Example 2. 240 mg (0.027mmol, based on the tungsten compound) of the solid catalyst described in Example 1 are suspended in 4.7 ccm (26.6 mmol) of the compound (CF$_3$)$_2$CFCH$_2$CH$_2$CH=CH$_2$ at room temperature and the mixture is shaken at 76° C. for 7 hours. 0.1 mol of tungsten compound is employed per 100 mol of (CF$_3$)$_2$CFCH$_2$CH$_2$CH=CH$_2$. The same reaction product as in Example 6 is formed. The total conversion of the starting substance is 97% after 7 hours (based on 100% possible conversion). 1,570 mol of the starting alkene are reacted per hour and per mol of tungsten compound.

EXAMPLE 9

120 mg (0.023 mmol, based on the tungsten compound) of the solid catalyst described in Example 6 are suspended in 10 ccm of heptane at 60° C. in a glass flask of 20 ccm capacity, 0.54 ccm (4.6 mmol) of 1,5-hexadiene and 0.82 ccm (4.6 mmol) of 4-(perfluoroisopropyl)-1-butene are added and the mixture is heated to 69° C. and shaken for 5 hours. 100 mol of 1,5-hexadiene are employed per 100 mol of 4-(perfluoroisopropyl)-1-butene, and 0.25 mol of tungsten compound is employed per 100 mol of the mixture of the two starting substances mentioned. After 5 hours, the reaction mixture formed is separated from the catalyst and analyzed by gas chromatography and by gas chromatography with direct subsequent mass spectroscopy (GC/MS analysis), the following values being determined:

| | |
|---|---|
| $(CF_3)_2CFCH_2CH_2CH=CH_2$ } starting compounds | 27.9% by wt. |
| $CH_2=CH-CH_2-CH_2-CH=CH_2$ | 5.3% by wt. |
| $(CF_3)_2CFCH_2CH_2CH=CHCH_2CH_2CF(CF_3)_2)$ | 7.8% by wt. |
| $(CF_3)_2CFCH_2CH_2CH=CH-CH_2CH_2-CH=CH_2$ | 27.3% by wt. |
| $(CF_3)_2CFCH_2CH_2CH=CH-CH_2CH_2-CH=CHCH_2CH_2CF(CF_3)_2$ | 6.5% by wt. |
| $(CF_3)_2CFCH_2CH_2CH=(CHCH_2CH_2CH=)_2CH_2$ | 12.0% by wt. |
| $(CF_3)_2CFCH_2CH_2CH=(CHCH_2CH_2CH=)_3CH_2$ | 2.8% by wt. |
| remainder | 10.4% by wt. |
| | 100% by wt. |

The remainder consists of a mixture of the following compounds:

$(CF_3)_2CFCH_2CH_2CH=(CHCH_2CH_2CH=)_yCHCH_2CH_2CF(CF_3)_2$ y=2 and 3

$(CF_3)_2CFCH_2CH_2CH=(CHCH_2CH_2CH=)_zCH_2$ z=4, 5 and 6.

As can be seen, the longer-chain alkenes which have 1 to 6 central —CH=CH— groups and carry perfluoroisopropyl groups either on one or on both chain ends are formed.

EXAMPLE 10

The procedure is analogous to Example 2. 130 mg (0.025 mmol, based on the tungsten compound) of a finely divided, solid catalyst obtained by reaction of a solid silicon dioxide-chromium(II) catalyst with the compound $(CO)_5W=C(phenyl)_2$, CO being split off, as described in "Angewandte Chemie", 100 (1988), pages 268 to 270, are suspended in 4 ccm of heptane at room temperature, and 0.9 ccm (5.2 mmol) or 4-perfluoroisopropyl-1-butene is added. The mixture is heated to 76° C., while stirring. 0.5 mol of tungsten compound is employed per 100 mol of 4-perfluoroisopropyl-1-butene. The decrease in the starting substance and the increase in the reaction product are monitored by gas chromatography during the reaction. After a reaction time of 1 hour the conversion is 26% by weight, which corresponds to a conversion rate of 52 mol of perfluoroalkylalkene per mol of tungsten compound. After a reaction time of 24 hours, the total yield is 55% by weight (based on 100% possible yield).

We claim:

1. A process for the reaction of a substituted hydrocarbon which contains at least one double bond using a tungsten-containing catalyst on a solid support, ethylene or an alkene being split off, to form a longer-chain substituted hydrocarbon which contains at least one central double bond, at 10° to 200° C., if necessary in the presence of an inert solvent, under normal atmospheric pressure, reduced pressure or the autogenous pressure of the reaction mixture, which comprises using, for the reaction, at least one alkene of the formula $$X-R_f(CH_2)_n-CH=CH-Z \qquad (I)$$

or $$CH_2F-(CH_2)_m-CH=CH-Z \qquad (II)$$

in which
$R_f$ is a straight-chain, branched or cyclic perfluoroalkylene radical having 1 to 18 carbon atoms,
m and n are each an integer from 1 to 10,
X is F, H, Cl, alkyl having 1 to 6 carbon atoms, or aryl having 6 to 10 carbon atoms and
Z is H, alkyl having 1 to 10 carbon atoms, arylalkyl having 7 to 11 carbon atoms, the radical $-(CH_2)_nR_fX$ or the radical $-(CH_2)_m-CH_2F$, in which, if only one compound is employed, this must have different substituents on the two sides of the —CH=CH— group.

2. The process as claimed in claim 1, wherein, in addition to at least one compound of the formula (I) or (II), at least one compound of the formula $$A-(CH_2)_t-CH=CH-E \qquad (III)$$

in which
A is H, —CH$_2$Cl, aryl having 6 to 10 carbon atoms or —CH=CH$_2$,
t is an integer from 1 to 10 and
E is H, alkyl having 1 to 10 carbon atoms or arylalkyl having 7 to 11 carbon atoms,
and the bonds at A and E can be closed to form a ring, is employed.

3. The process as claimed in claim 1, wherein the catalyst is built up from a solid support, which essentially consists of silicon dioxide, aluminum oxide or a mixture of these two oxides, onto which tungsten is bonded, via O atoms or via O atoms and chromium, as a complex compound which has a bond between tungsten and carbon.

4. The process as claimed in claim 1, wherein a catalyst of the formula $$\begin{array}{c} L_s^1 \\ | \\ R_3-W\equiv C-R^4 \\ | \\ L_s^2 \end{array} \qquad (IV)$$

in which
- R$_3$ is Cl, —CH$_2$—C(CH$_3$)$_3$, —O—C(CH$_3$)$_3$, —S—C(CH$_3$)$_3$ or —NG$_2$, in which G is an alkyl group having 1 to 4 carbon atoms or the benzyl radical,
- R$^4$ is a straight-chain, branched or cyclic alkyl group having 1 to 6 carbon atoms, a trialkylsilyl group, the alkyl radicals of which each comprise 1 to 3 carbon atoms, or a benzyl, phenyl, tolyl or naphthyl group,
- L$^1$ is a trialkylphosphine, trialkylphosphine oxide or ethylene glycol dialkyl ether, the alkyl groups of which contain 1 to 4 carbon atoms,
- L$^2$ is a trialkylphosphine, trialkylphosphine oxide, trialkylphosphonium chloride or tetraalkylammonium chloride, the alkyl groups of which contain 1 to 4 carbon atoms, with the proviso that R is Cl if L$^2$ is a trialkylphosphonium or tetralkylammonium chloride, and
- s is zero or 1, is employed.

5. The process as claimed in claim 1, wherein at least one compound of the formula (I) in which X is F and Z is H is employed.

6. The process as claimed in claim 1, wherein at least one compound of the formula (II) in which A is —CH═CH$_2$ and E is H is employed.

7. A process as claimed in claim 1, wherein said temperature is from 30° to 150° C.

8. A process as claimed in claim 1, wherein said temperature is from 50° to 120° C.

9. A process as claimed in claim 1, wherein said compound of Formula I is selected from the group consisting of (CF$_3$)$_2$CF—(CH$_2$)$_2$—CH═CH$_2$, (C$_6$)F$_{13}$—CH$_2$—CH═CH$_2$, (C$_8$)F$_{17}$—(CH$_2$)$_2$—CH═CH$_2$,

CHF$_2$)—(CF$_2$)$_3$—(CH$_2$)$_2$—CH═CH$_2$,

CClF$_2$CF$_2$—(CH$_2$)$_3$—CH═CH$_2$,

C$_2$H$_5$—(CF$_2$)$_2$—(CH$_2$)$_4$—CH═CH$_2$,

Phenyl-(CF$_2$)$_2$—(CH$_2$)$_2$—CH═CH$_2$,

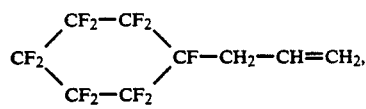

C$_4$F$_9$—(CH$_2$)$_2$—CH═CH—(CH$_2$)$_2$C$_4$F$_9$,

C$_6$F$_{13}$—CH$_2$—CH═CH—CH═CH—CH$_2$-Phenyl, and

CHF$_2$—(CF$_2$)$_2$—(CH$_2$)$_2$—CH═CH—(CH$_2$-)$_2$—(CF$_2$)$_2$—CHF$_2$.

10. A process as claimed in claim 1, wherein said compound of Formula II is selected from the group consisting of

CH$_2$F—(CH$_2$)$_3$—CH═CH$_2$,

CH$_2$F—(CH$_2$)$_6$—CH═CH—C$_2$H$_5$,

CH$_2$F—(CH$_2$)$_8$—CH═CH—CH$_2$-Phenyl, and,

CH$_2$F—(CH$_2$)$_2$—CH═(CH$_2$)$_2$—CH$_2$F.

11. A process as claimed in claim 2, wherein said compound of Formula III is selected from the group consisting of

CH$_3$—(CH$_2$)$_7$—CH═CH$_2$,

CH$_2$Cl—CH$_2$—CH═CH$_2$,

Phenyl-CH$_2$CH$_2$—CH═CH$_2$,

CH$_2$═CH—(CH$_2$)$_2$—CH═CH$_2$,

CH$_2$Cl—CH$_2$—CH═CH—CH$_2$—CH$_2$Cl,

Phenyl-CH$_2$—CH═CH—CH$_2$-Phenyl,

CH$_3$—(CH$_2$)$_4$—CH═CH—CH$_3$,

CH$_3$—(CH$_2$)$_7$—CH═CH—(CH$_2$)$_7$—CH$_3$,

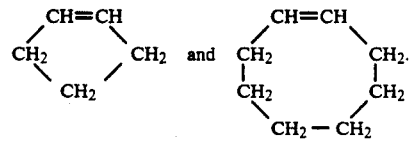

12. A process as claimed in claim 4, wherein said compound of Formula IV is selected from the group consisting of (CH$_3$OCH$_2$CH$_2$OCH$_3$)Cl$_3$W═C—C(CH$_3$)$_3$,

[(CH$_3$)$_3$C—CH$_2$—]$_3$W═C—C(CH$_3$)$_3$,

[(CH$_3$)$_3$C—O—]$_3$W═C—C(CH$_3$)$_3$,

[(CH$_3$)$_3$C—S—]$_3$W═C—C(CH$_3$)$_3$,

[(CH$_3$)$_2$N—]$_3$W═C—C(CH$_3$)$_3$,

[(CH$_3$)$_3$P]Cl$_3$W═C—C(CH$_3$)$_3$,

[(C$_2$H$_5$)$_3$P]Cl$_3$W═C—C(CH$_3$)$_3$,

[(C$_2$H$_5$)$_3$PO]Cl$_3$W═C—C(CH$_3$)$_3$,

[(C$_2$H$_5$)$_3$P][(C$_2$H$_5$)$_3$PO]Cl$_3$W═C—C(CH$_3$)$_3$,

[(C$_2$H$_5$)$_3$PH]$^+$[Cl$_4$W═C—C(CH$_3$)$_3$]$^-$,

[(C$_2$H$_5$)$_4$N]$^+$[Cl$_4$W═C—C(CH$_3$)$_3$]$^-$,

[(C$_2$H$_5$)$_4$N]$^+$  [Cl$_4$W≡C—C(CH$_3$)$_3$]$^-$,
(C$_2$H$_5$)$_3$P (CH$_3$OCH$_2$CH$_2$OCH$_3$)Cl$_3$W≡C—CH$_3$,

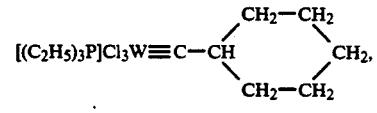

[(CH$_3$)$_3$P]Cl$_3$W═C—CH$_2$-Phenyl,
[(CH$_3$)$_3$C—CH$_2$]$_3$—W═C-Phenyl and

[(CH$_3$)$_3$C—CH$_2$]$_3$—W═C—Si(CH$_3$)$_3$.

* * * * *